(12) United States Patent
Ariyama et al.

(10) Patent No.: US 7,172,341 B2
(45) Date of Patent: Feb. 6, 2007

(54) IMAGING APPARATUS AND SUBJECT MOVING DEVICE

(75) Inventors: Naoki Ariyama, Tokyo (JP); Ryosuke Fujimoto, Tokyo (JP); Akira Izuhara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/295,264

(22) Filed: Dec. 5, 2005

(65) Prior Publication Data

US 2006/0120515 A1    Jun. 8, 2006

(30) Foreign Application Priority Data

Dec. 6, 2004    (JP) ............... 2004-352821

(51) Int. Cl.
*A61B 6/04* (2006.01)
(52) U.S. Cl. ................. 378/209; 378/20
(58) Field of Classification Search ........... 378/20, 378/208, 209; 5/601; 600/415
See application file for complete search history.

(56) References Cited

U.S. PATENT DOCUMENTS

| 3,997,926 | A |   | 12/1976 | England |
|---|---|---|---|---|
| 4,761,000 | A |   | 8/1988 | Fisher et al. |
| 5,131,105 | A |   | 7/1992 | Harrawood et al. |
| 5,205,004 | A |   | 4/1993 | Hayes et al. |
| 5,825,843 | A | * | 10/1998 | Kobayashi ............ 378/20 |
| 6,353,949 | B1 |   | 3/2002 | Falbo |
| 6,381,780 | B1 |   | 5/2002 | Nose et al. |
| 6,955,464 | B1 | * | 10/2005 | Tybinkowski et al. ...... 378/209 |
| 2004/0141591 | A1 |   | 7/2004 | Izuhara |

FOREIGN PATENT DOCUMENTS

JP    2004-173756    6/2004

OTHER PUBLICATIONS

Akira Izuhara et al.; "Subject Moving Apparatus and Imaging Apparatus"; U.S. Appl. No. 11/200,812; filed Aug. 10, 2005; 23 pgs.

* cited by examiner

*Primary Examiner*—Edward J. Glick
*Assistant Examiner*—Hoon Song
(74) *Attorney, Agent, or Firm*—Carl B. Horton; Armstrong Teasdale LLP

(57) ABSTRACT

With the object of, when a table unit is moved downward as viewed in a vertical direction by use of an actuator, smoothly moving the table unit and enhancing operability, when the actuator moves the table unit from a first position in the vertical direction to a downward second position, a pressure controller adjusts the amount of fluid held in the actuator on the basis of the first position of the table unit, detected by a position detector to thereby control pressure based on the fluid.

10 Claims, 11 Drawing Sheets

IMAGING APPARATUS AND SUBJECT MOVING DEVICE

CROSS REFERENCE TO RELATED APPLICATIONS

This application claims the benefit of Japanese Application No. 2004-352821 filed Dec. 6, 2004.

BACKGROUND OF THE INVENTION

The present invention relates to an imaging apparatus and a subject moving device thereof, and particularly to an imaging apparatus for imaging an image of a subject moved to an imaging space, and a subject moving device thereof.

In an imaging apparatus such as an X-ray CT (Computed Tomography) apparatus or the like, a subject moving device moves a subject to an imaging space, and a scanning gantry scans the subject moved to the imaging space to obtain row data of the subject. An image about a tomographic plane of the subject is generated by reconstruction on the basis of the obtained row data. Such an X-ray CT apparatus has been utilized for a wide range of uses such as a medical use, an industrial use, etc.

The scanning gantry in the X-ray CT apparatus includes an X-ray tube and an X-ray detector. The X-ray tube applies X rays to the subject and the X-ray detector detects the X rays transmitted through the subject to generate projection data of the subject. Here, the scanning gantry rotates the X-ray tube and the X-ray detector with a body axial direction of the subject as an axis. The scanning gantry applies the X rays from the periphery of the subject and acquires projection data corresponding to a plurality of view directions as row data of an image.

In the X-ray CT apparatus, the subject moving device includes a table section and a table moving section. The table section supports the subject and the table moving section moves the table section into an imaging space of a scanning gantry (refer to, for example, a patent document 1).

[Patent Document 1] Japanese Unexamined Patent Publication No. 2004-173756

There is a case in which an actuator is used in the above table moving section to move the table section. The actuator is of, for example, a hydraulic actuator. The actuator holds oil-like fluid inside a cylinder and expands and contracts over its entire length according to the pressure of the fluid held thereinside to move the table section. The actuator adjusts a flow rate of the fluid held in the cylinder using, for example, a plunger type proportional controlled valve to thereby control pressure based on the fluid held thereinside. Thus, the actuator expands and contracts and hence changes in its entire length, thereby moving the table section. Using the actuator in the table moving section makes it possible to move the table section quietly and smoothly and realize miniaturization, durability, reliability, a cost reduction and the like of the apparatus.

However, there was a case in which when the table section was moved downward as viewed in a vertical direction, it became difficult to move the table section smoothly. There were, for example, cases in which when the table section was moved downward up to a reference position as viewed in the vertical direction, the table section was moved to a position placed further downward beyond the reference position and a shock was given to the subject due to a descending operation. This principally results from the fact that since the pressure based on the fluid held in the cylinder of the actuator differs according to the position of the table section at the start of the movement thereof downward, the flow rate of the fluid adjusted by the proportional controlled valve is different from a reference value. In addition to the case referred to above, there was a case in which since the pressure based on the fluid lying inside the cylinder differed according to the weight of a subject to be imaged or photographed, it became difficult to move the table section smoothly in like manner. There was also a case in which since the pressure based on the fluid lying inside the cylinder differed due to changes with time and variations in the apparatus, it became difficult to move the table section smoothly in like manner.

Therefore, the above imaging apparatus encountered difficulties in handling it with ease and caused a reduction in its operability.

SUMMARY OF THE INVENTION

Thus, an object of the present invention is to provide an imaging apparatus capable of enhancing operability and realizing the smooth movement of a table section, and a subject moving device thereof.

In order to attain the above object, there is provided an imaging apparatus of the present invention, which has a table unit supporting a subject and a table mover for moving the table unit to an imaging space and which images the subject supported by the table unit moved to the imaging space by the table mover, comprising a position detector for detecting a position in a vertical direction, of the table unit, wherein the table mover includes a bottom plate provided downward from the table unit as viewed in the vertical direction, a support bar having a first shaft provided at one end thereof, which is pivotally supported by the bottom plate, and a second shaft provided at the other end thereof, which is pivotally supported by the table unit, the support bar supporting the table unit, an actuator having a third shaft provided at one end thereof, which is pivotally supported by the bottom plate, and a fourth shaft provided at the other end thereof, which is pivotally supported by the support bar, the actuator expanding and contracting according to pressure of fluid held thereinside to thereby rotate the support bar with the first shaft as the center to move the table unit in the vertical direction, and a pressure controller for adjusting a flow rate of the fluid held in the actuator to thereby control pressure based on the fluid held in the actuator, and wherein when the actuator moves the table unit from a first position in the vertical direction to a downward second position, the position detector detects the first position where the movement of the table unit is started by the actuator, and the pressure controller adjusts the amount of the fluid held in the actuator on the basis of the first position detected by the position detector to thereby control the pressure.

In order to attain the above object, there is provided a subject moving device comprising a table unit for supporting a subject, a table mover for moving the table unit in a vertical direction, and a position detector for detecting a position in the vertical direction, of the table unit, wherein the table mover includes a bottom plate provided downward from the table unit as viewed in the vertical direction, a support bar having a first shaft provided at one end thereof, which is pivotally supported by the bottom plate, and a second shaft provided at the other end thereof, which is pivotally supported by the table unit, the support bar supporting the table unit, an actuator having a third shaft provided at one end thereof, which is pivotally supported by the bottom plate, and a fourth shaft provided at the other end thereof, which is pivotally supported by the support bar, the actuator expanding and contracting according to pressure of fluid held thereinside to thereby rotate the support bar with the first shaft as the center to move the table unit in the vertical direction, and a pressure controller for adjusting a flow rate of the fluid held in the actuator to thereby control pressure based on the fluid held in the actuator, and wherein when the actuator moves the table unit from a first position in the vertical direction to a downward second position, the position detector detects the first position where the movement of the table unit is started by the actuator, and the pressure controller adjusts the amount of the fluid held in the actuator on the basis of the first position detected by the position detector to thereby control the pressure.

According to the present invention, there can be provided an imaging apparatus capable of enhancing operability and realizing the smooth movement of a table section and a subject moving device thereof.

Further objects and advantages of the present invention will be apparent from the following description of the preferred embodiments of the invention as illustrated in the accompanying drawings.

DETAILED DESCRIPTION OF THE INVENTION

Embodiments of the present invention will be explained.

<FIRST EMBODIMENT>

Figure 1:
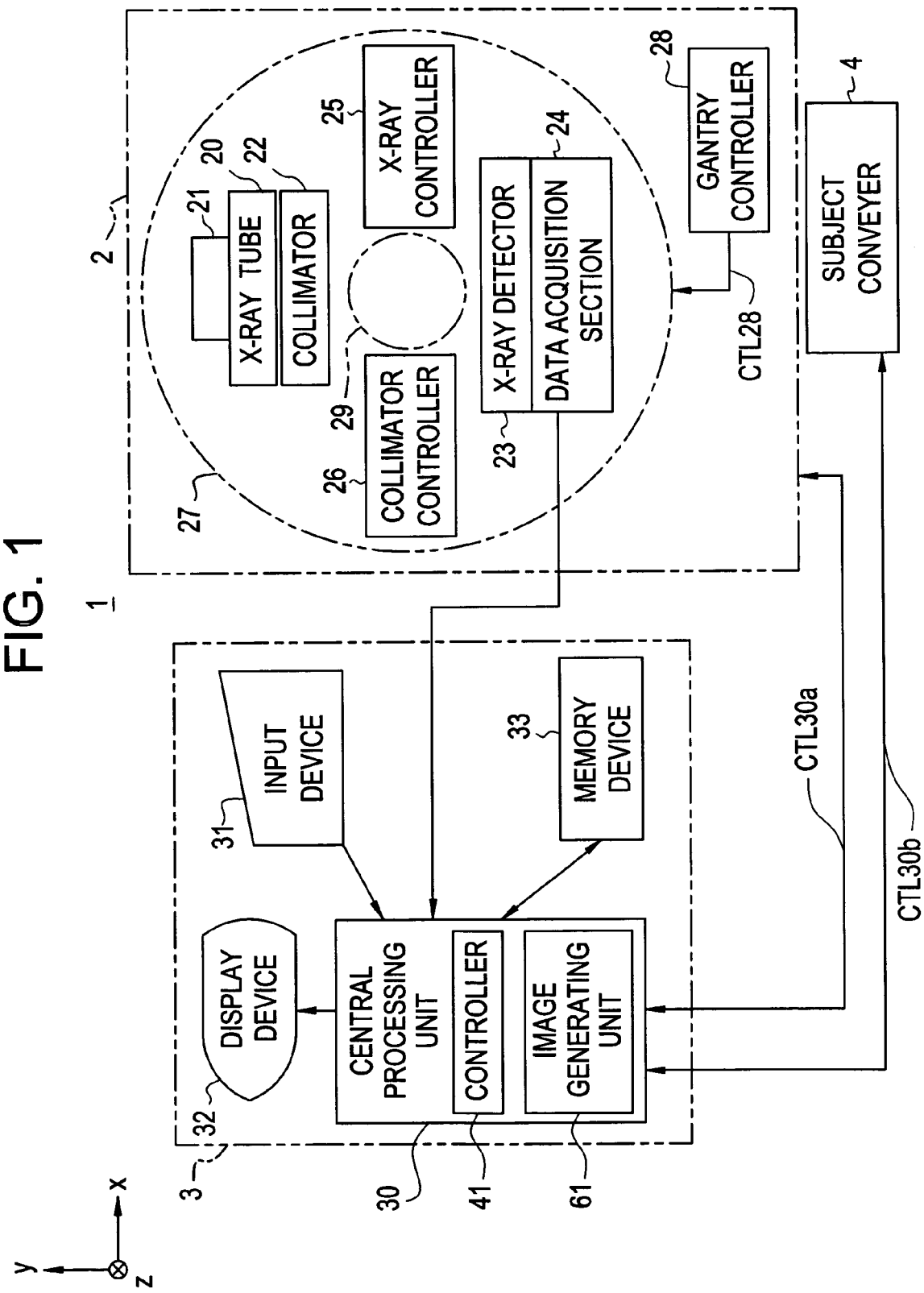
FIG. 1 is a block diagram showing an overall construction of an X-ray CT apparatus illustrative of a first embodiment according to the present invention.
Figure 2:
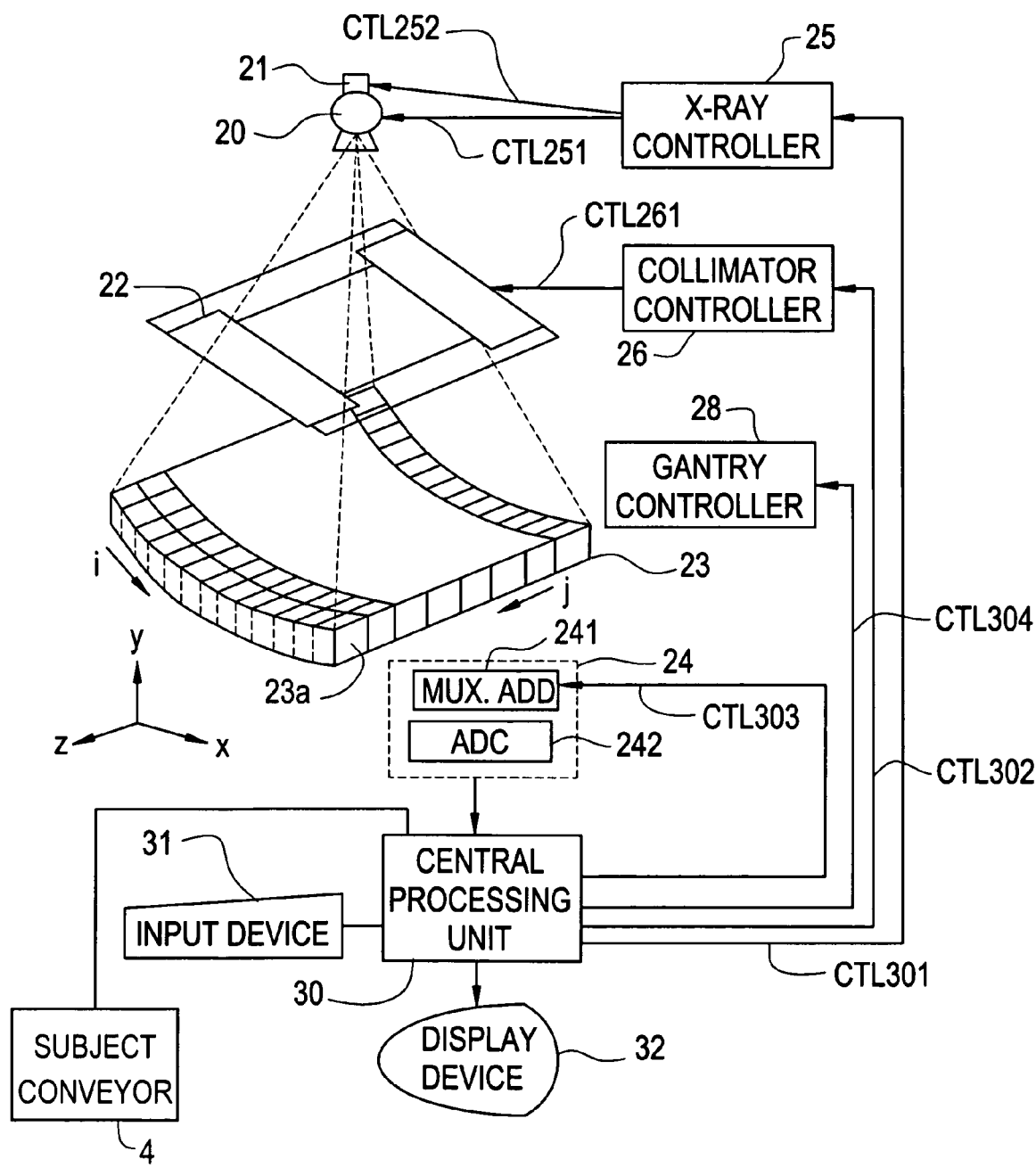
FIG. 2 is a configuration diagram depicting an essential part of the X-ray CT apparatus illustrative of the first embodiment according to the present invention.

FIG. 1 is a block diagram showing an overall construction of an X-ray CT apparatus 1 used as an imaging apparatus illustrative of a first embodiment according to the present invention, and FIG. 2 is a configuration diagram showing an essential part of the X-ray CT apparatus 1 of the embodiment according to the present invention, respectively.

As shown in FIG. 1, the X-ray CT apparatus 1 includes a scanning gantry 2, an operation console 3 and a subject moving device or moving section 4.

The scanning gantry 2 has an X-ray tube 20, an X-ray tube moving section 21, a collimator 22, an X-ray detector 23, a data acquisition section 24, an X-ray controller 25, a collimator controller 26, a rotational section 27 and a gantry controller 28. The scanning gantry 2 scans a subject supported by a table section 101 moved to an imaging space 29 by a table moving section 102 of the subject moving device 4 to be described later to thereby obtain projection data of the subject as row data.

Figure 3:
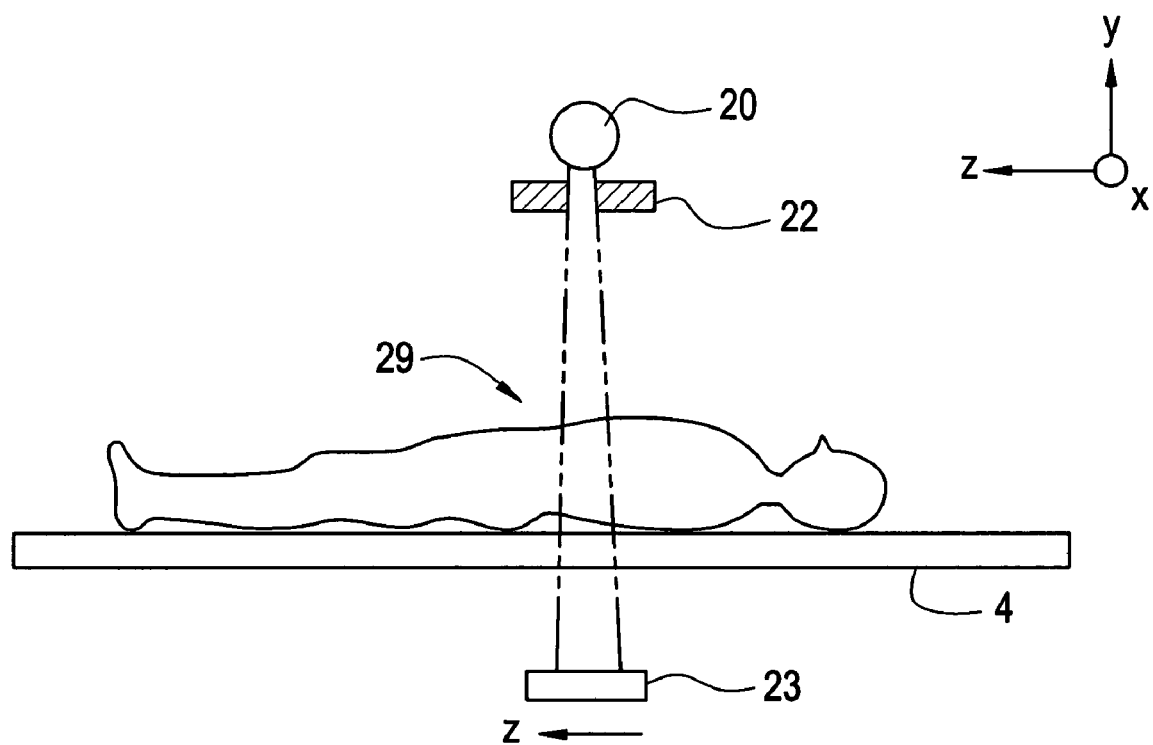
FIG. 3 is a diagram showing the relationship of a layout among an X-ray tube, a collimator and an X-ray detector in a scanning gantry of the X-ray CT apparatus of the first embodiment according to the present invention.

FIG. 3 is a diagram showing the relationship of a layout among the X-ray tube 20, the collimator 22 and the X-ray detector 23 in the scanning gantry 2.

In the scanning gantry 2, as shown in FIG. 3, the X-ray tube 20 and the X-ray detector 23 are disposed so as to interpose therebetween the imaging space 29 in which the subject is carried and imaging is performed. The collimator 22 is disposed so as to shape X rays from the X-ray tube 20.

The respective parts of the scanning gantry 2 will be explained.

The X-ray tube 20 is of, for example, a rotating anode type and applies X rays. As shown in FIG. 2, the X-ray tube 20 applies X rays of predetermined intensity to an imaging region of the subject via the collimator 22, based on a control signal CTL251 outputted from the X-ray controller 25. The X rays radiated from the X-ray tube 20 are shaped in the form of, for example, a cone by the collimator 22 and applied to the X-ray detector 23. The X-ray tube 20 rotates about the subject by the rotational section 27 with a body axial direction z of the subject as the axis in order to apply the X rays from view directions as viewed in the periphery of the subject.

As shown in FIG. 2, the X-ray tube moving section 21 moves the center of radiation of the X-ray tube 20 in the body axial direction z of the subject in the imaging space 29 of the scanning gantry 2 on the basis of a control signal CTL252 outputted from the X-ray controller 25.

As shown in FIG. 2, the collimator 22 is disposed between the X-ray tube 20 and the X-ray detector 23. The collimator 22 is constituted of plates respectively provided two by two in a channel direction i and a row direction j. The collimator 22 moves the two plates provided in the respective directions independently on the basis of a control signal CTL261 outputted from the collimator controller 26 and blocks or cuts off the X rays radiated from the X-ray tube 20 as viewed in the respective directions to shape the X rays in cone form, thereby adjusting the range of radiation of the X rays.

The X-ray detector 23 detects the X rays radiated from the X-ray tube 20 and transmitted through the subject and generates projection data of the subject. The X-ray detector 23 rotates about the subject together with the X-ray tube 20 by the rotational section 27. And the X-ray detector 23 detects the X rays radiated from the periphery of the subject and transmitted through the subject to generate projection data.

The X-ray detector 23 comprises a plurality of detecting elements 23a as shown in FIG. 2. In the X-ray detector 23, the detecting elements 23a are two-dimensionally laid out in array form in the channel direction i extending along the direction in which the X-ray tube 20 rotates around the subject by virtue of the rotational section 27 with the body axial direction z of the subject as the center and in the row direction j extending along the direction of a rotational axis used as a central axis when the X-ray tube 20 is rotated by the rotational section 27. The X-ray detector 23 has a cylindrical plane bent in a concave form, which is formed by the plurality of two-dimensionally arranged detecting elements 23.

The detecting elements 23a that constitute the X-ray detector 23 has, for example, scintillators (not shown) which transduce the detected X rays into light, and photo diodes (not shown) which convert the light transduced by the scintillators to electrical charges. The X-ray detector 23 is configured as a solid-state detector. Incidentally, each of the detecting elements 23a is not limited to above but may be, for example, a semiconductor detecting element using cadmium telluride (CdTe) or the like or an ion chamber type detecting element 23a using a xenon (Xe) gas.

The data acquisition section 24 is provided to collect or acquire projection data from the X-ray detector 23. The data acquisition section 24 collects the projection data detected by the respective detecting elements 23a of the X-ray detector 23 and outputs the same to the operation console 3. As shown in FIG. 2, the data acquisition section 24 has a selection/addition switching circuit (MUX, ADD) 241 and an analog-digital converter (ADC) 242. The selection/addition switching circuit 241 selects the projection data detected by the detecting elements 23a of the X-ray detector 23 in response to a control signal CTL303 outputted from the central processing unit 30 or adds up them by a change in combination thereof and outputs the result of addition to the analog-digital converter 242. The analog-digital converter 242 converts the projection data selected or added up in an arbitrary combination at the selection/addition switching circuit 241 from an analog signal to a digital signal and outputs it to the central processing unit 30.

As shown in FIG. 2, the X-ray controller 25 outputs a control signal CTL251 to the X-ray tube 20 in response to a control signal CTL301 outputted from the central processing unit 30 to control the application of the X rays. The X-ray controller 25 controls, for example, a tube current value or the like supplied to the X-ray tube 20. Further, the X-ray controller 25 outputs a control signal CTL252 to the X-ray tube moving section 21 in response to the control signal CTL301 outputted from the central processing unit 30 and controls the center of radiation of the X-ray tube 20 so as to move it in the body axial direction z.

As shown in FIG. 2, the collimator controller 26 outputs a control signal CTL261 to the collimator 22 in response to a control signal CTL302 outputted from the central processing unit 30 and controls the collimator 22 in such a manner that it shapes the X rays radiated from the X-ray tube 20.

As shown in FIG. 1, the rotational section 27 is cylindrical in shape and is formed with the imaging space 29 thereinside. The rotational section 27 rotates around the subject in response to a control signal CTL28 outputted from the gantry controller 28 with the body axial direction z of the subject in the imaging space 29 as the center. The rotational section 27 is equipped with the X-ray tube 20, X-ray tube moving section 21, collimator 22, X-ray detector 23, data acquisition section 24, X-ray controller 245 and collimator controller 26. The relationship of position between the subject carried in the imaging space 29 and the respective portions relatively changes in the direction of rotation of the rotational section 27. By rotating the rotational section 27, the X-ray tube 20 is capable of applying the X rays to the subject from the periphery of the subject every plural view directions. The X-ray detector 23 is able to detect the X rays transmitted through the subject every their view directions. The rotational section 27 is tilted in response to the control signal CTL28 outputted from the gantry controller 28. The rotational section 27 is inclined along the body axial direction z with the isocenter of the imaging space 29 as the center.

As shown in FIGS. 1 and 2, the gantry controller 28 outputs the control signal CTL28 to the rotational section 27, based on a control signal CTL304 outputted from the central processing unit 30 of the operation console 3 and controls the rotational section 27 so that it is rotated and tilted.

The operation console 3 will be explained.

As shown in FIG. 1, the operation console 3 includes the central processing unit 30, an input device 31, a display device 32 and a memory device 33.

The central processing unit 30 is constituted of, for example, a computer and includes a controller 41 and an image generating unit 61 as shown in FIG. 1.

The controller 41 is provided to control the respective portions. For example, the controller 41 accepts a scan condition inputted to the input device 31 by an operator and outputs a control signal CTL30a to the respective portions, based on the scan condition to execute a scan. Described specifically, the controller 41 outputs a control signal CTL30b to the subject moving device 4 and allows the subject moving device 4 to move the subject to the imaging space 29. Then, the controller 41 outputs a control signal CTL304 to the gantry controller 28 to rotate the rotational section 27 of the scanning gantry 2. Further, the controller 41 outputs a control signal CTL301 to the X-ray controller 25 such that X rays are radiated from the X-ray tube 20. The controller 41 outputs a control signal CTL302 to the collimator controller 26 and thereby controls the collimator 22 to shape the X rays. The controller 41 outputs a control signal CTL303 to the data acquisition section 24 and controls the data acquisition section 24 to collect projection data obtained by the detecting elements 23a of the X-ray detector 23.

The image generating unit 61 reconstructs an image of a tomographic plane of the subject on the basis of the projection data collected by the data acquisition section 24 of the scanning gantry 2 referred to above. The image generating unit 61 performs pre-treatment such as sensitivity correction, beam hardening correction, etc. on projection data from plural view directions based on an axial scan, for example. Thereafter, the image generating unit 61 reconstructs the so-processed data by a filtered back projection method to reconstruct and generate the image of the tomographic plane of the subject.

The input apparatus 31 of the operation console 3 is constituted of input devices such as a keyboard, a mouse, etc. The input apparatus 31 inputs various information such as a scan condition, information about the subject and the like to the central processing unit 30 on the basis of operator's input operations.

The display device 32 displays the image about the tomographic plane of the subject reconstructed by the image generating unit 61, based on a command issued from the central processing unit 30.

The memory device 33 is made up of a memory and stores therein various data such as each image of the subject reconstructed by the image generating unit 61, and programs and the like. In the memory device 33, the data stored therein are accessed by the central processing unit 30 as needed.

The subject moving device 4 will be explained.

The subject moving device 4 is provided to move the subject between the inside and outside of the imaging space 29. The subject moving device 4 carries out the operation of moving the subject, based on the control signal CTL30b sent from the central processing unit 30.

Figure 4:
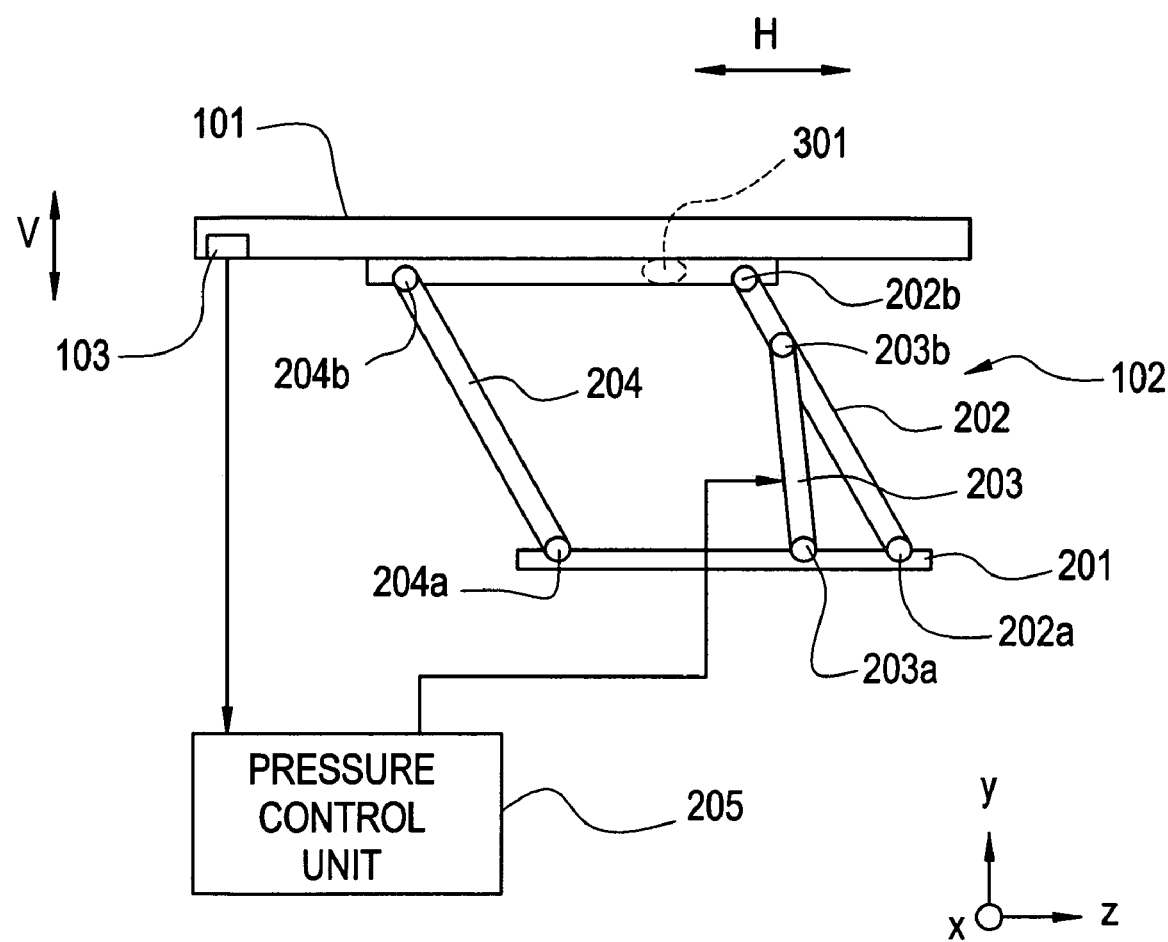
FIG. 4 is a configuration diagram illustrating the construction of a subject moving device in the X-ray CT apparatus of the first embodiment according to the present invention.
Figure 5:
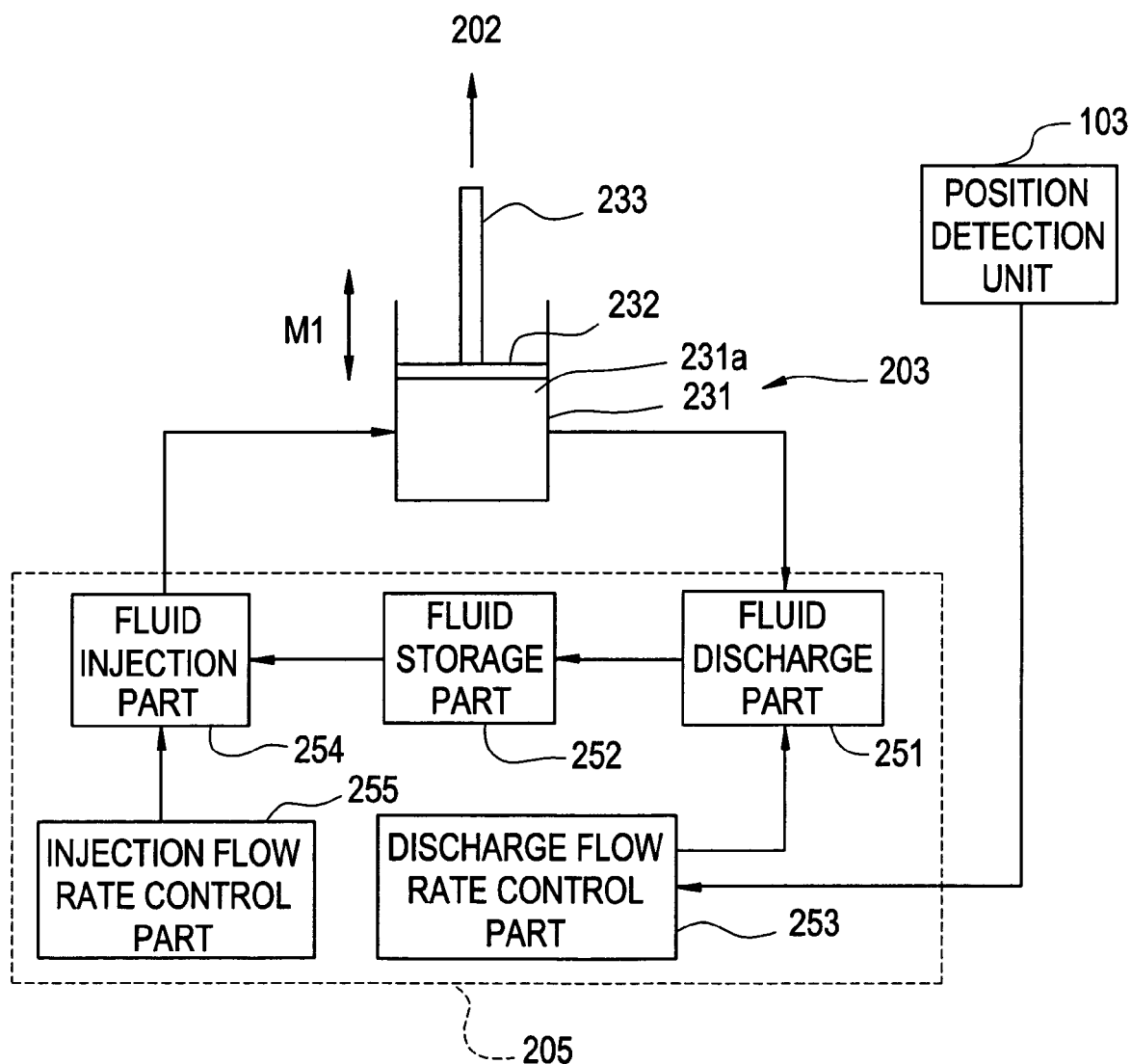
FIG. 5 is a block diagram showing the construction of an essential part of the subject moving device in the X-ray CT apparatus of the first embodiment according to the present invention.

FIGS. 4 and 5 are diagrams showing the subject moving device 4. Here, FIG. 4 is a configuration diagram showing the construction of the subject moving device 4. FIG. 5 is a block diagram showing the construction of an essential part of the subject moving device 4.

As shown in FIG. 4, the subject moving device 4 has a table section 101, a table moving section 102 and a position detection unit 103. The respective portions will be explained sequentially.

The table section 101 is provided to support the subject. The table section 101 includes a table and is formed with a mounting surface on which the subject is placed. As shown in FIG. 4, the table section 101 is moved by the table moving section 102 in both directions of a horizontal direction H extending along the body axial direction z of the subject placed on the mounting surface and a vertical direction V corresponding to a gravitational direction orthogonal to a horizontal plane, and carried in the imaging space 29.

The table moving section 102 is provided to move the table section 101. The table moving section 102 moves the table section 101 between the inner and outer sides of the imaging space 29. As shown in FIG. 4, the table moving section 102 includes a bottom or base plate 201, a first support bar 202, an actuator 203, a second support bar 204, a pressure control unit 205 and a horizontal moving part 301.

The base plate 201 is provided below as viewed in the vertical direction from the table section 101 and fixed.

The first support bar 202 is a bar-like link member and includes a first shaft 202a provided at one end thereof and a second shaft 202b provided at the other end thereof. The first support bar 202 is formed such that the first shaft 202a provided at one end is pivotally supported by the base plate 201, and is formed so as to be rotatably moved about the first shaft 202a between the first support bar 202 and the base plate 201. Further, the first support bar 202 is formed such that the second shaft 202b provided at the other end is pivotally supported by the table section 101, and is formed so as to be rotatably moved about the second shaft 202b between the first support bar 202a nd the table section 101. Thus, the first support bar 202 supports the table section 101 by the second shaft 202b provided at the other end thereof.

The actuator 203 is a device mechanically operated using energy based on fluid. As shown in FIG. 4, the actuator 203 moves the table section 101 in the vertical and horizontal directions V and H. The actuator 203 includes a third shaft 203a provided at one end thereof and a fourth shaft 203b provided at the other end thereof. The actuator 203 is formed such that the third shaft 203a provided at one end thereof is pivotally supported by the base plate 201, and is formed so as to be rotatably moved about the third shaft 203a between the actuator 203 and the base plate 201. The actuator 203 is formed such that the fourth shaft 203b provided at the other end thereof is pivotally supported by the first support bar 202, and is formed so as to be rotatably moved about the fourth shaft 203b between the actuator 203 and the first support bar 202. In the present embodiment, the fourth shaft 203b provided at the other end is pivotally supported so as to be placed on the table section 101 side as viewed from the center of the first support bar 202. The actuator 203 expands and contracts according to the pressure of fluid held thereinside to rotatably move the first support bar 202 about the first shaft 202a, thereby rotatably moving the table section 101 in the vertical and horizontal directions V and H respectively. At this time, the actuator 203 is also rotatably moved about the third shaft 203a along the direction of rotational motion of the table section 101.

As shown in FIG. 5, the actuator 203 includes a cylinder 231, a piston 232 and a coupling rod 233.

The cylinder 231 holds fluid 231a thereinside and holds the piston 232 moved forward and backward alternately inside the cylinder 231 according to the pressure of the fluid 231a. The cylinder 231 is pivotally supported by the base plate 201 at the third shaft 203a. The cylinder 231 holds, for example, oil as the fluid 231a. In the cylinder 231, the amount of the fluid 231a held thereinside is adjusted by the pressure control unit 205, so that the pressure of the fluid 231a is controlled.

The piston 232 is accommodated in the cylinder 231. The piston 232 is moved forward and backward alternately inside the cylinder 231 according to the pressure of the fluid 231a held in the cylinder 231. As indicated by arrow M1 shown in FIG. 5 by way of example, the piston 232 is reciprocated inside the cylinder 231. When the amount of the fluid 231a held in the cylinder 231 increases so that its pressure is made high, the piston 232 is moved along the direction in which the fluid 231a increases in the cylinder 231, thereby moving the table section 101 upward as viewed in the vertical direction V. When the amount of the fluid 231a held in the cylinder 231 is reduced so that its pressure is lowered, the piston 232 is moved to the side of holding of the fluid 231 a in the cylinder 231 to shift the table section 101 downward as viewed in the vertical direction V.

The coupling rod 233 is provided so as to couple between the piston 232 and the first support bar 202. The coupling rod 233 is pivotally supported by the first support bar 202 at the fourth shaft 203b. The reciprocating operation of the piston 232 is transferred to the first support bar 202 to rotatably move the first support bar 202.

As shown in FIG. 4, the second support bar 204 of the table moving section 102 is a bar-like link member and includes a fifth shaft 204a provided at one end thereof and a sixth shaft 204b provided at the other end thereof. The second support bar 204 is formed such that the fifth shaft 204a provided at one end is pivotally supported by the base plate 201, and is formed so as to be rotatably moved about the fifth shaft 204a between the second support bar 204 and the base plate 201. Further, the second support bar 204 is formed such that the sixth shaft 204b provided at the other end is pivotally supported by the table section 101, and is formed so as to be rotatably moved about the sixth shaft 204b between the second support bar 204 and the table section 101. Thus, the second support bar 204 supports the table section 101 by the sixth shaft 204b provided at the other end thereof. The second support bar 204 is identical in length to the first support bar 202. Even when the table section 101 is moved in the vertical direction V, the second support bar 204 is formed so as to be parallel with the first support bar 202 as viewed in it longitudinal direction.

The pressure control unit 205 of the table moving section 102 adjusts the flow rate of the fluid 231a held in the cylinder 231 of the actuator 203 to thereby control the pressure produced by the fluid 231a of the actuator 203. In the present embodiment, when the table section 101 is moved from a first position as viewed in the vertical direction V to a second position as viewed downward by use of the actuator 203, the pressure control unit 205 adjusts the flow rate of the fluid 231a in the actuator 203 based on the first position of the table section 101, detected by the position detection unit 103 to control the pressure of the fluid 231a.

As shown in FIG. 5, the pressure control unit 205 includes a fluid discharge part 251, a fluid storage part 252, a discharge flow rate control part 253, a fluid injection part 254 and an injection flow rate control part 255.

The fluid discharge part 251 is coupled to the cylinder 231 of the actuator 203 and formed so as to discharge the fluid 231a held in the cylinder 231. The fluid discharge part 251 includes a proportional controlled valve at which the degree of opening of its discharge port is adjusted in proportion to a voltage applied thereto. The fluid discharge part 251 adjusts the flow rate at the discharge of the fluid 231a held in the actuator 203, using the proportional controlled valve to thereby control the pressure based on the fluid 231a. When the table section 101 is moved from the first position as viewed in the vertical direction V to the second position as viewed downward by using the actuator 203, the fluid discharge part 251 accepts a discharge flow rate determined by the discharge flow rate control part 253, based on the first position and adjusts the degree of opening of the discharge port by application of the voltage to the proportional controlled valve so as to correspond to the discharge flow rate determined by the discharge flow rage control part 253, and discharges the fluid 231a held in the cylinder 231 of the actuator 203 to the fluid storage part 252.

The fluid storage part 252 includes a tank which stores the fluid 231a therein. The fluid storage part 252 is coupled to the fluid discharge part 251. When the fluid discharge part 251 discharges the fluid 231a from the cylinder 231 of the actuator 203, the fluid storage part 252 stores the discharged fluid 231a in the tank. The fluid storage part 252 is coupled to the fluid injection part 254. When the fluid injection part 254 injects the fluid 231a into the cylinder 231 of the actuator 203, the fluid storage part 252 supplies the fluid 231a stored in the tank to the fluid injection part 254.

The discharge flow rate control part 253 is provided to adjust a discharge flow rate at the time that the fluid discharge part 251 discharges the fluid 231a held in the cylinder 231 of the actuator 203. The discharge flow rate control part 253 is constituted of, for example, a computer. When the table section 101 is moved from the first position as viewed in the vertical direction V to the second position as viewed downward by using the actuator 203, the discharge flow rate control part 253 accepts information about the first position corresponding to a start position at the descending operation of the table section 101 from the position detection unit 103. Then, the discharge flow rate control part 253 adjusts a flow rate at which the fluid 231a of the actuator 203 is discharged, so as to correspond to the first position. Described specifically, since a large force is unnecessary upon opening the valve where the first position corresponding to the start position for the descending operation is placed in a high position, a voltage of a low value is applied to adjust the flow rate at which the fluid 231a of the actuator 203 is discharged. On the other hand, since a large force is necessary upon opening of the valve as compared with the high position where the first position corresponding to the start position for the descending operation is of a low position, a voltage of a higher value is applied to adjust the flow rate at which the fluid 231a of the actuator 203 is discharged.

The fluid injection part 254 is coupled to the cylinder 231 of the actuator 203 and formed so as to inject fluid 231a into the cylinder 231, based on a command issued from the injection flow rate control part 255. The fluid injection part 254 includes a pump driven by a motor and delivers the fluid 231a held in the fluid storage part 252 to the cylinder 231 of the actuator 203 by the pump. When the table section 101 is moved upward as viewed in the vertical direction V, the fluid injection part 254 supplies the fluid 231a stored in the fluid storage part 252 to the cylinder 231 of the actuator 203 and increases the pressure of the fluid 231a of the cylinder 231.

The injection flow rate control part 255 is provided to adjust an injection flow rate at which the fluid injection part 254 injects the fluid 231a into the cylinder 231 of the actuator 203. For example, the injection flow rate control part 255 is configured of, for example, a computer. The injection flow rate control part 255 controls a voltage for driving the pump of the fluid injection part 254 and delivers the fluid 231a stored in the fluid storage part 252 to the cylinder 231 of the actuator 203 by means of the pump.

The horizontal moving part 301 of the table moving section 102 is formed so as to move the table section 101 in the horizontal direction H. The horizontal moving part 301 is equipped with a roller type drive mechanism (not shown) and drives a roller by a motor (not shown) to move the table section 101 in the horizontal direction H.

The position detection unit 103 shown in FIG. 4 is formed so as to detect the position of the table section 101 as viewed in the vertical direction V. The position detection unit 103 includes, for example, a non-contact optical potentiometer. In the position detection unit 103, the optical potentiometer is provided at the end of the table section 101 as shown in FIG. 4, for example. As shown in FIG. 5, the position detection unit 103 outputs the result of the position in the vertical direction V, of the table section 101 to the discharge flow rate control part 253 of the pressure control unit 205. In the present embodiment, when the actuator 203 moves the table section 101 from the first position in the vertical direction V to the second position as viewed downward, the position detection unit 103 detects the first position at which the movement of the table section 101 is started by the actuator 203, and outputs the result of detection to the pressure control unit 205.

Incidentally, the X-ray CT apparatus according to the present embodiment corresponds to an imaging apparatus of the present invention. The scanning gantry 2 employed in the present embodiment corresponds to a scan section of the present invention. The X-ray tube 20 employed in the present embodiment corresponds to a radiation unit of the present invention. The X-ray detector 23 employed in the present embodiment corresponds to a detection unit of the present invention. The table section 101 employed in the present embodiment corresponds to a table unit of the present invention. The table moving section 102 employed in the present embodiment corresponds to a table mover of the present invention. The imaging space 29 employed in the present embodiment corresponds to an imaging space of the present invention. The table section 101 employed in the present embodiment corresponds to a table unit of the present invention. The table moving section 102 employed in the present embodiment corresponds to a table mover of the present invention. The position detection unit 103 employed in the present embodiment corresponds to a position detector of the present invention. The base plate 201 employed in the present embodiment corresponds to a bottom plate of the present invention. The first support bar 202 employed in the present embodiment corresponds to a support bar of the present invention. The actuator 203 employed in the present embodiment corresponds to an actuator of the present invention. The pressure control unit 205 employed in the present embodiment corresponds to a pressure controller of the present invention. The cylinder 231 employed in the present embodiment corresponds to a cylinder of the present invention. The piston 232 employed in the present embodiment corresponds to a piston of the present invention. The coupling rod 233 employed in the present embodiment corresponds to a coupling rod of the present invention.

The operation of the X-ray CT apparatus 1 according to the present embodiment will be explained below.

Figure 6:
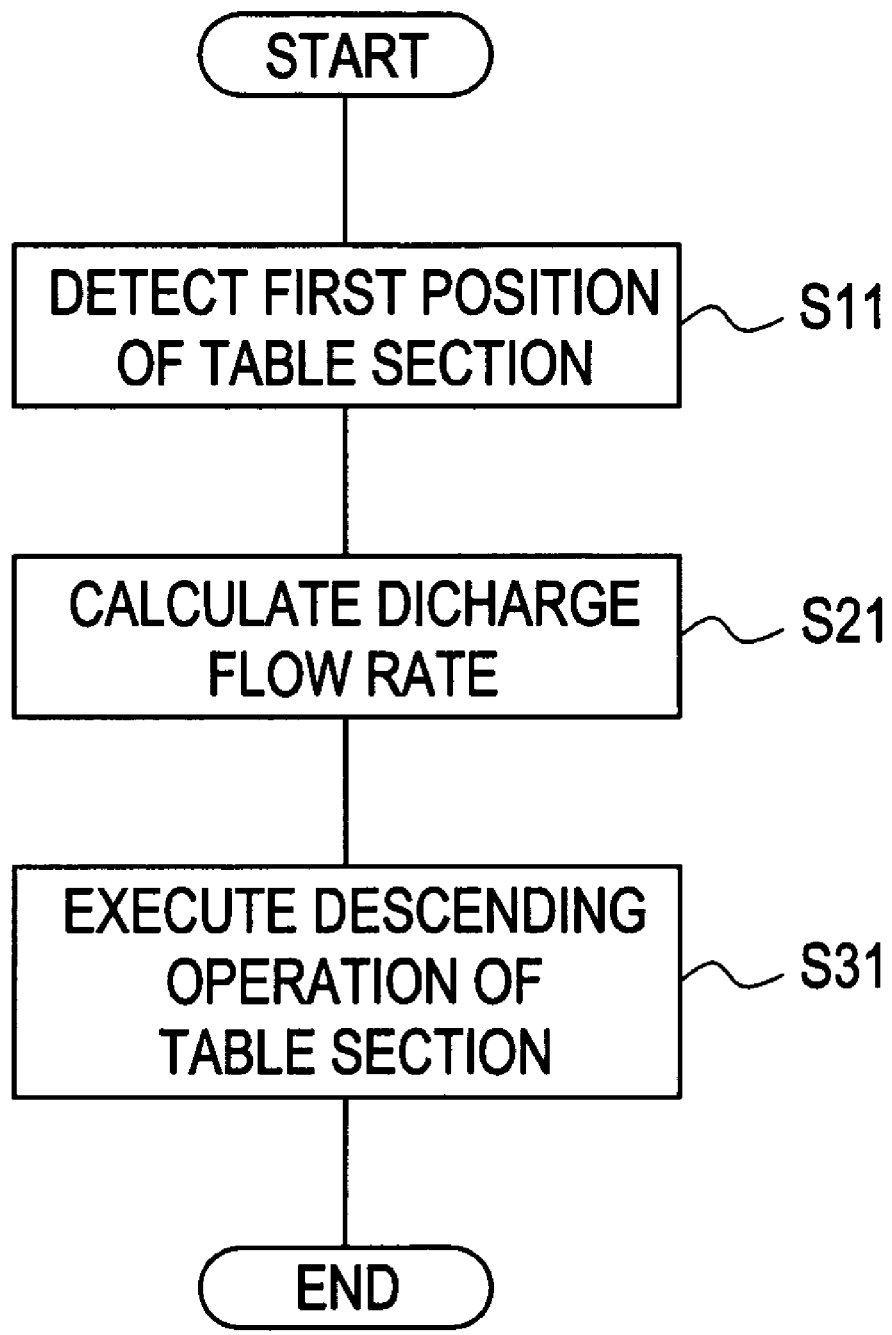
FIG. 6 is a flowchart depicting the operation of moving a table section downward as viewed in a vertical direction.

FIG. 6 is a flowchart showing the operation of moving the table section 101 downward as viewed in the vertical direction H in the X-ray CT apparatus 1 of the present embodiment.

When the table section 101 is moved downward as viewed in the vertical direction V as shown in FIG. 6, a first position of the table section 101 is first detected (S11).

Here, the position detection unit 103 detects the first position corresponding to a start position when the table section 101 is moved downward as viewed in the vertical direction V. The position detection unit 103 outputs the result of the position in the vertical direction V, of the table section 101 to the discharge flow rate control part 253 of the pressure control unit 205.

Next, a flow rate at which the fluid 231a held in the actuator 203 is discharged is calculated (S21).

Here, the discharge flow rate control part 253 of the pressure control unit 205 calculates a discharge flow rate at the time that the fluid discharge part 251 discharges the fluid 231a held in the cylinder 231 of the actuator 203. Described specifically, when the table section 101 is moved from the first position as viewed in the vertical direction V to a second position as viewed downward by using the actuator 203, the discharge flow rate control part 253 acquires information about the first position corresponding to a start position at the descending position of the table section 101 from the position detection unit 103. The discharge flow rate control part 253 adjusts a flow rate at which the fluid 231a of the actuator 203 is discharged, so as to correspond to the first position corresponding to the start position for the descending operation.

Figure 7A:
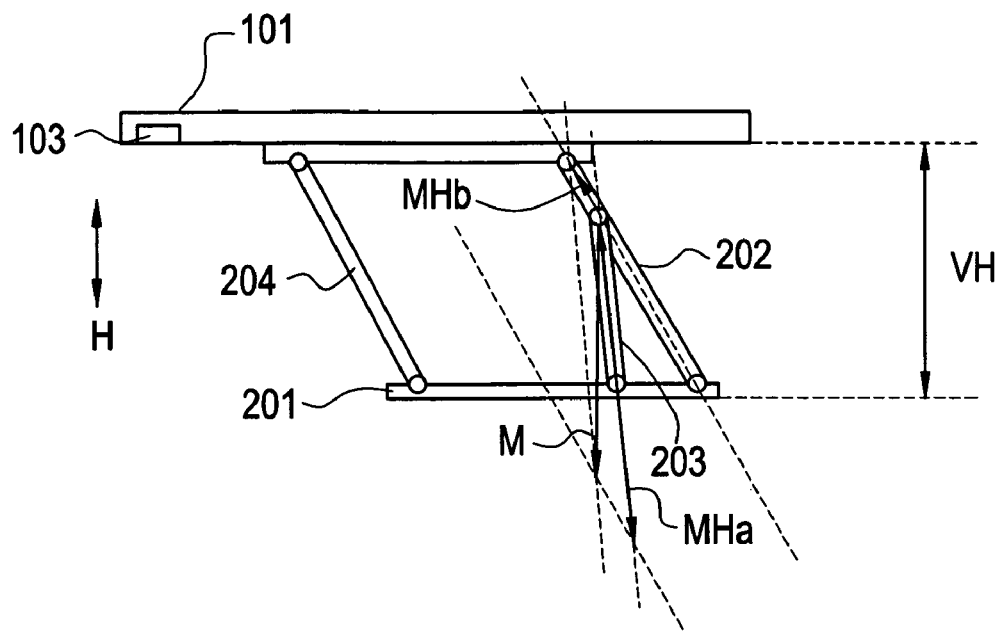
FIG. 7 is a diagram showing the manner in which pressure applied to fluid of an actuator differs according to the height of the table section in the X-ray CT apparatus of the first embodiment according to the present invention.
Figure 7B:
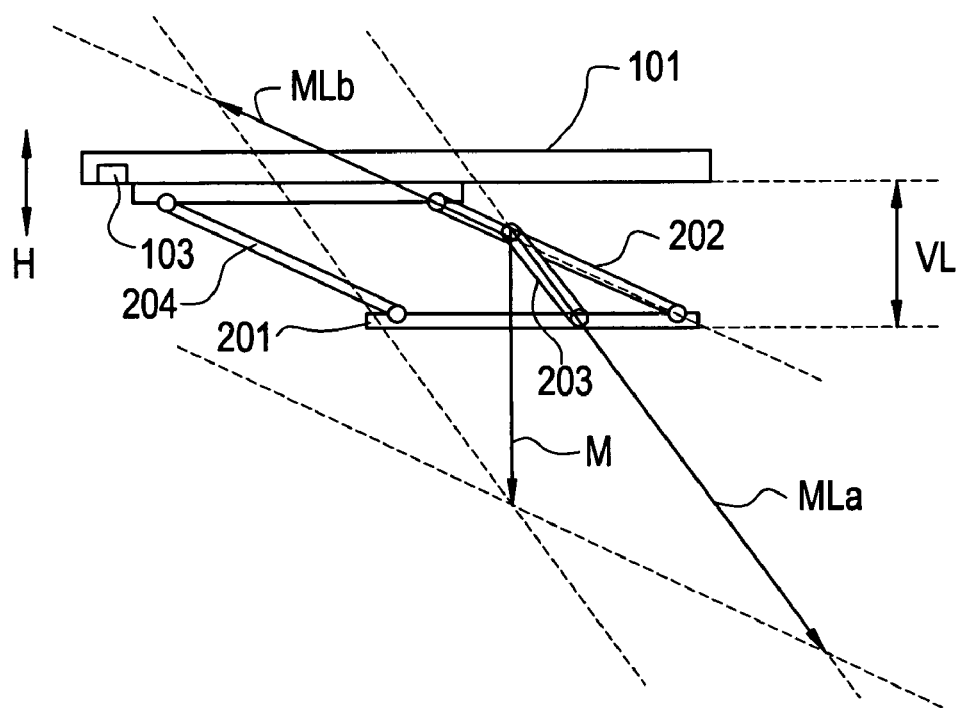
Figure 8:
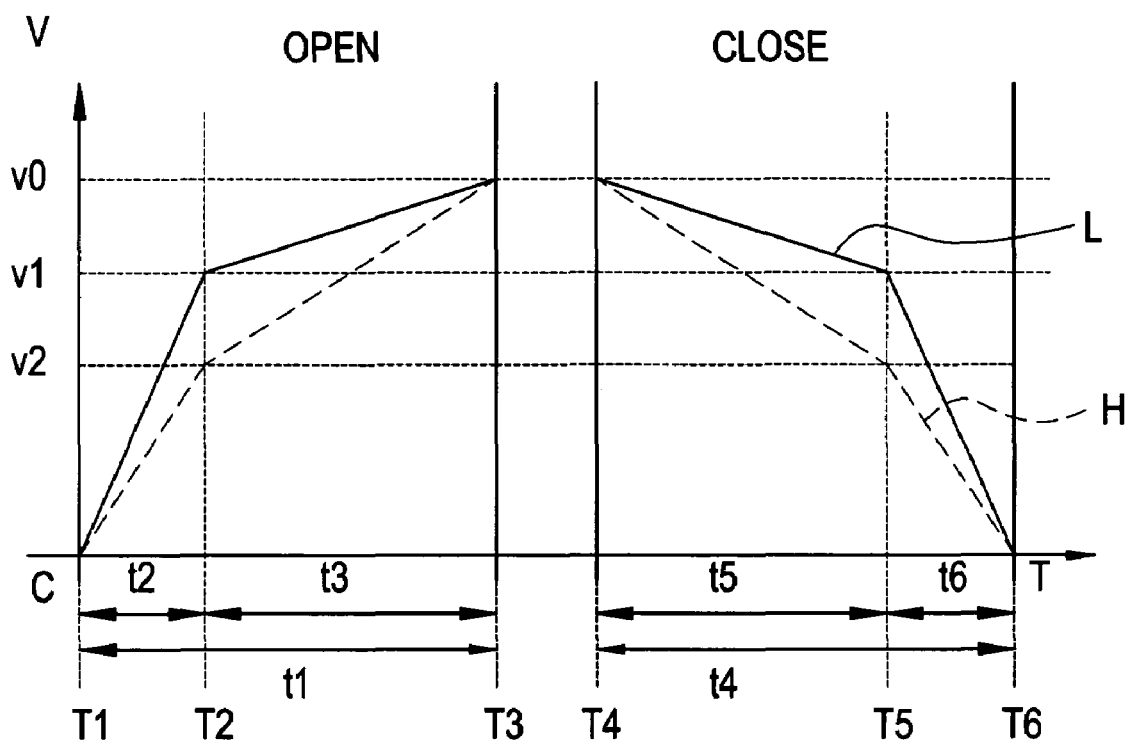
FIG. 8 is a diagram showing the relationship between a voltage V applied to a proportional controlled valve of a fluid discharge unit and time T at a descending operation in association with profiles of discharged flow rates calculated by a discharge flow rate control part in the X-ray CT apparatus of the first embodiment according to the present invention.

FIGS. 7 and 8 are diagrams for describing flow rates calculated by the discharge flow rate control part 253.

Here, FIG. 7 is a diagram showing the manner in which pressure applied to the fluid 231a of the actuator 203 differs according to the height of the table section 101. In FIG. 7, FIG. 7(A) shows where the first position corresponding to the descending start position of the table section 101 is placed in a high position VH. FIG. 7(B) shows where the first position corresponding to the descending start position of the table section 101 is placed in a low position VL. On the other hand, FIG. 8 shows the relationship between a voltage V applied to the proportional controlled valve of the fluid discharge part 251 and time T at the descending operation in association with profiles of the discharged flow rates calculated by the discharge flow rate control part 253.

When moments identical in magnitude to each other are applied in the vertical direction H as shown in FIG. 7, the magnitude of a moment MLa applied in the direction in which the piston 232 of the actuator 203 is reciprocated, when the table section 101 is placed in the low position VL as shown in FIG. 7(B), is larger than that of a moment MHa applied in the direction in which the piston 232 of the actuator 203 is moved forward and backward alternately, when the table section 101 is placed in the high position VH as shown in FIG. 7(A). Therefore, the pressure of the fluid 231a held in the cylinder 231 of the actuator 203 differs according to the height of the table section 101.

Therefore, a large force is not necessary upon the opening of the valve where the first position corresponding to the start position for the descending operation is placed in the high position as shown in FIG. 8. Therefore, a voltage of a low value is applied to adjust a flow rate. On the other hand, since a large force is necessary upon opening the valve as compared with the high position where the first position corresponding to the start position for the descending operation is placed in the low position, a voltage of a higher value is applied to adjust a flow rate. Thus, even when the first position corresponding to the start position is placed in the low position VL and the moment MLa applied in the direction in which the piston 232 of the actuator 203 is reciprocated, is large, the actuator 203 generates a moment opposite to the moment MLa.

Described specifically, as shown in FIG. 8, voltage profiles H and L are determined in such a manner that the voltage value at the time that the descending start position is placed in the high position VH reaches a voltage value v2 lower than a voltage value v1 at the time that the descending start position is placed in the low position VL, at a time T2 at which a predetermined time t2 has elapsed since a time T1 at which the operation of descending the table section 101 is started. At a time T3 at which a time t3 has further elapsed since the start time T1, the same voltage value v0 is applied and voltage profiles H and L are determined such that the degree of opening of the proportional controlled valve is brought to the same fully-opened state where the descending start position is placed in both of the high and low positions VH and VL.

When the operation of descending the table section 101 is stopped, voltage profiles H and L are determined in such a manner that the voltage value at the time that the descending start position is placed in the high position VH reaches the voltage value v2 lower than the voltage value v1 at the time that the descending start position is placed in the low position VL at a time T5 at which a time t5 has elapsed since a time T4 at which the same voltage value v0 is applied. At a time T6 at which a time t4 has further elapsed since the time T4 at which the same voltage value v0 is applied, voltage profiles H and L are determined such that the degree of opening of the proportional controlled valve is brought to the same fully-opened state without application of any voltage where the descending start position is placed in both of the high and low positions VH and VL.

The descending operation of the table section 101 is next carried out (S31).

Here, the fluid discharge part 251 first accepts voltage profiles corresponding to a discharge flow rate determined by the discharge flow rate control part 253 on the basis of the first position where the operation of descending the table section 101 is started. Then, a voltage is applied to the proportional controlled valve to adjust the degree of opening of the discharge port on the basis of the voltage profiles associated with the discharge flow rate determined by the discharge flow rate control part 253. The fluid 231a held in the cylinder 231 of the actuator 203 is discharged to the fluid storage part 252 to move the table section 101 downward as viewed in the vertical direction H.

According to the present embodiment as described above, when the actuator 203 moves the table section 101 from the first position in the vertical direction V to the second position as viewed downward, the pressure control unit adjusts the amount of the fluid 231a held in the actuator 203 on the basis of the first position of the table section 101, which is detected by the position detection unit 103 to thereby control the pressure based on the fluid 231a. Therefore, the present embodiment makes it easy to smoothly move the table section 101 upon moving the table section 101 downward as viewed in the vertical direction V. Thus, it is possible to prevent the table section from being moved to a position placed further downward beyond a reference position in the vertical direction upon moving the table section downward up to the reference position and to suppress the application of a shock to the subject due to the descending operation. Accordingly, the present embodiment makes it easy to handle the apparatus and is hence capable of enhancing operability. As a result, it is possible to move the table section quietly and smoothly and realize miniaturization, durability, reliability, a cost reduction and the like of the apparatus. It is also possible to enhance safety relative to the subject.

<SECOND EMBODIMENT>

Figure 9:
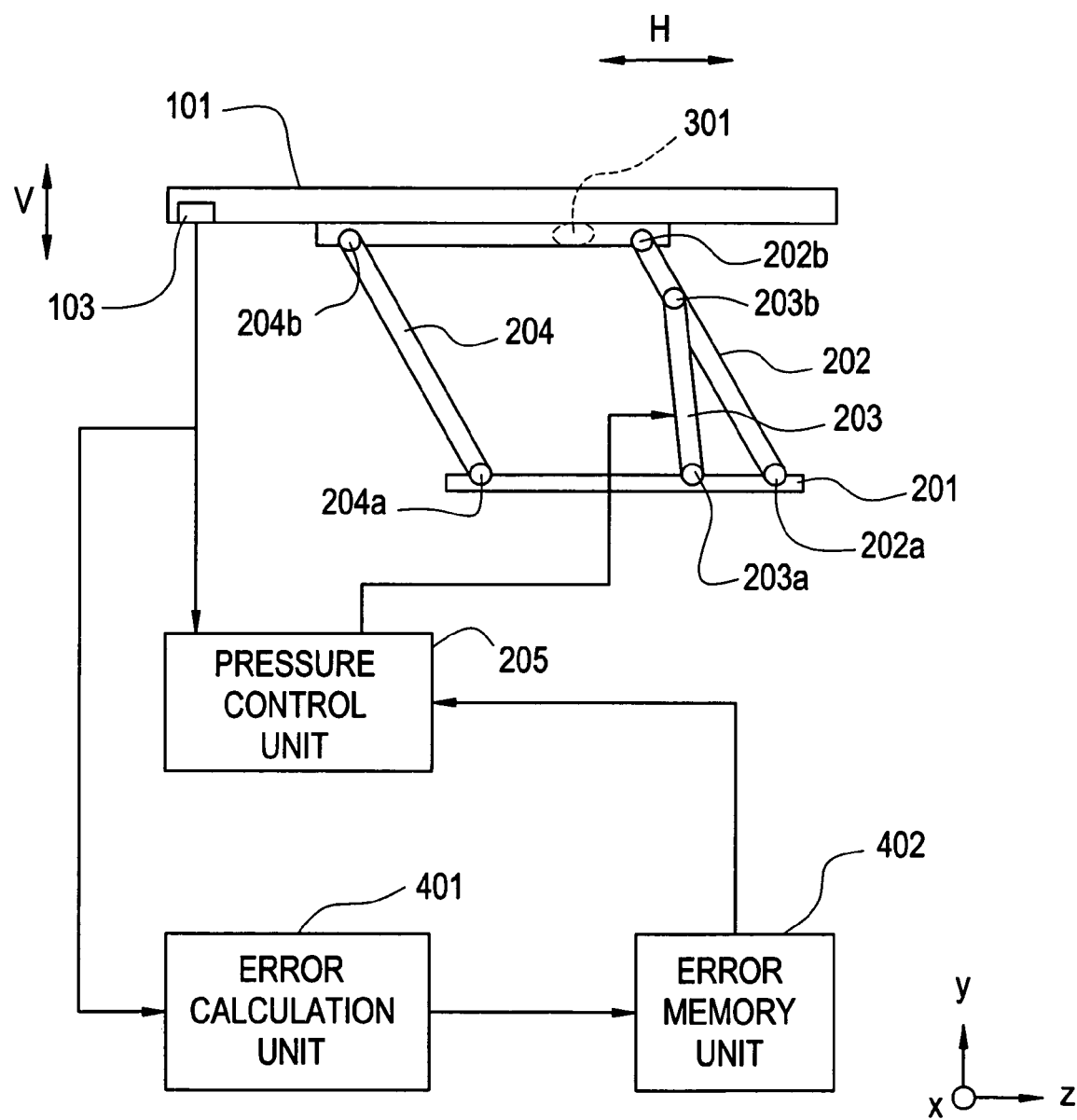
FIG. 9 is a block diagram showing the construction of an essential part of an X-ray CT apparatus illustrative of a second embodiment according to the present invention.

FIG. 9 is a block diagram showing the construction of an essential part of an X-ray CT apparatus illustrative of a second embodiment according to the present invention.

As shown in FIG. 9, the present embodiment is similar to the first embodiment except that it has an error calculation unit 401 and an error memory unit 402, and the function of the pressure control unit 205 differs. Therefore, dual components are given the same reference numerals and their explanations are therefore omitted. Incidentally, the error calculation unit 401 employed in the present embodiment corresponds to an error calculator of the present invention. The error memory unit 402 employed in the present embodiment corresponds to an error memory of the present invention. The pressure control unit 205 of the present embodiment corresponds to a pressure controller of the present invention.

The respective portions different from the first embodiment will be explained below.

The error calculation unit 401 is configured of a computer. When a table moving section 102 designates a table section 101 from a first position as viewed in a vertical direction H to a second position as viewed downward on the basis of a control signal CTL30b outputted from a central processing unit 30 and moves the table section 101 thereto, the error calculation unit 401 calculates an error of a position where the table section is moved to a third position different from the designated second position. For example, the error calculation unit 401 calculates an error of a position where the table section is moved to a third position placed further downward beyond the designated second position. Here, when the table moving section 102 moves the table section 101 downward as viewed in the vertical direction H, the error calculation unit 401 acquires information about the corresponding first position equivalent to a start position at the downward movement of the table section 101 from a position detection unit 103. The position detection unit 103 detects information about a third position corresponding to the position where the table section 101 has actually stopped after its descending operation. The result of its detection is acquired from the position detection unit 103. Using a second position corresponding to a reference position at the time that the table moving section 102 stops the table section under its descending operation on the basis of the control signal CTL30b outputted from the central processing unit 30, and the third position acquired from the position detection unit 103, the error calculation unit 401 thereafter calculates an error corresponding to a differential value between the second position and the third position. The error calculation unit 401 outputs information about the first position at the descending operation thereof and information about an error corresponding to the differential value between the second position and the third position to the error memory unit 402. That is, when the table moving section 102 descends the table section 101, the error calculation unit 401 calculates a distance overrun from the second position corresponding to the reference position where the table section is stopped by its descending operation to the third position and outputs information about the overrun distance to the error memory unit 402 as an error for the descending operation.

The error memory unit 402 is constituted of a memory and stores a plurality of errors calculated by the error calculation unit 401. Here, the error memory unit 402 stores the information about the first position corresponding to the start position at the descending operation and the second position corresponding to the reference position, the information about the error corresponding to the differential value between the second position corresponding to the reference position where the table section is stopped upon its descending operation, and the third position corresponding to the position where the table section is actually stopped, and the information in which the pressure control unit 205 controls the pressure of the fluid 231a of the actuator 203 upon the descending operation, all of which are outputted from the error calculation unit 401, in association with one another respectively. In the present embodiment, the error memory unit 402 receives the information about the distance overrun from the second position corresponding to the reference position at which the table section 101 is stopped due to the descending operation to the third position, from the error calculation unit 401 as information about the error at the descending operation each time the operation of descending the table section 101 by the table moving section 102 is carried out. Further, the error memory unit 402 stores the information about the error therein at any time as error history information in association with the respective information referred to above.

When the table moving section 102 moves the table section 101 downward, the pressure control unit 205 adjusts the amount of the fluid 231a held in the actuator 203, based on the error information stored in the error memory unit 402 to control the pressure. For instance, when the operation of descending the table section 101 from the first position to the second position is carried out at a first time G, the pressure control unit 205 acquires error information at the past second time K at the time that a descending operation similar to that at the first time G is carried out, from the history information about the plural errors stored in the error memory unit 402. The pressure control unit 205 adjusts the flow rate of the fluid 231a held in the actuator 203 in such a way that the error at the past second time K becomes small, thereby controlling the pressure. Described specifically, at the first time G, the discharge flow rate control part 253 of the pressure control unit 205 first acquires a command for moving the table section 101 from the first position as viewed in the vertical direction V to the second position as viewed downward from the central processing unit 30. The discharge flow rate control part 253 acquires the error information at the past second time K at which the descending operation similar to that at the first time G is carried out, from the error history information stored in the error memory unit 402. Thereafter, the discharge flow rate control part 253 corrects a profile for the discharge flow rate of the fluid 231a discharged from the cylinder 231 of the actuator 203 at the past second time K in such a manner that the error at the past second time K becomes small, and calculates the profile as a profile for the discharge flow rate at the first time. Then, the profile for the discharge flow rate calculated by the discharge flow rate control part 253 is outputted to the fluid discharge part 251. The fluid discharge part 251 applies a voltage to the proportional controlled valve in association with the discharge flow rate to adjust the degree of opening of the discharge port, thereby adjusting the pressure of the fluid 231a of the actuator 203.

Figure 10:
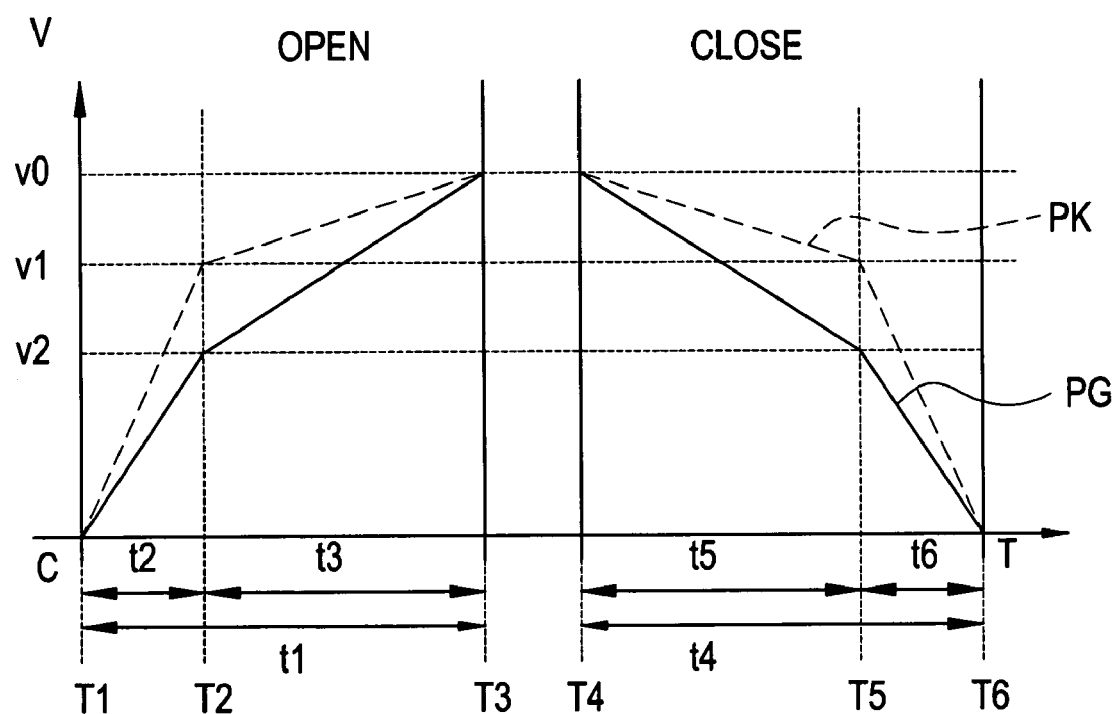
FIG. 10 is a diagram showing voltage profiles in which voltages are applied to a proportional controlled valve of a fluid discharge unit in association with profiles of discharged flow rates calculated by a discharge flow rate control part in the X-ray CT apparatus of the second embodiment according to the present invention.

FIG. 10 is a diagram showing each voltage profile at the time that each of voltages is applied to the proportional controlled valve of the fluid discharge part 251, in association with the profile for the discharge flow rate calculated by the discharge flow rate control part 253. In a manner similar to FIG. 8, FIG. 10 shows the relationship between a voltage v applied to the proportional controlled valve of the fluid discharge part 251 and time T at the descending operation and illustrates a voltage profile PG at the first time G and a voltage profile PK at the second time K.

When the table section is overrun from the second position corresponding to the reference position to the downward third position due to a descending operation at the past second time K as shown in FIG. 10, the voltage profile PG at the present first time G rather than the voltage profile PK at the second time K is calculated in such a manner that a low voltage is applied, to suppress its overrun by increasing the pressure of the fluid 231a of the actuator 203 as compared with the past second time K. That is, the opening of the proportional controlled valve at the descending operation at the first time G is adjusted so as to become smaller than the opening of the proportional controlled valve at the descending operation at the second time K to thereby adjust the flow rate of the fluid 231a of the actuator 203 to control its pressure.

Described specifically, as shown in FIG. 10, the corresponding voltage profile PG is determined in such a manner that at a time T2 at which a predetermined time t2 has elapsed since a time T1 at which the operation of descending the table section 101 is started, the voltage value at the descending operation at the present first time G reaches a voltage value v1 higher than a voltage value v2 at the descending operation at the past second time K. That is, the corresponding voltage profile PG is calculated in such a manner that the degree of opening of the proportional controlled valve at the descending operation at the present first time G becomes larger than that at the descending operation at the past second time K. At a time T3 at which a time t3 has further elapsed since the start time T1, the same voltage value v0 is applied and the voltage profile PG is determined in such a manner that the degree of opening of the proportional controlled valve is brought to the same fully-opened state.

Upon stopping the operation of descending the table section 101, as shown in FIG. 10, the corresponding voltage profile PG is determined in such a manner that at a time T5 at which a time t5 has further elapsed since a time T4 at which the same voltage value v0 is applied, the voltage value at the descending operation at the present first time G reaches a voltage value v1 higher than a voltage value v2 at the descending operation at the past second time K. At a time T6 at which a time t4 has further elapsed since the time T4 at which the same voltage value v0 is applied, voltage profiles H and L are determined without application of any voltage in such a manner that the degree of opening of the proportional controlled valve is brought to the same fully-opened state.

In the present embodiment as described above, when the table moving section 102 moves the table section 101 from the first position to the downward second position, the error calculation unit 401 calculates the error at the time that it is moved to the third position different from the second position in the vertical direction H, from the result of detection by the position detection unit 103. The error memory unit 402 stores therein the error calculated by the error calculation unit 401. Thereafter, the pressure control unit 205 adjusts the amount of the fluid 231a held in the actuator 203 on the basis of the error stored in the error memory unit 402 to thereby control its pressure. Therefore, even when the pressure based on the fluid 231a of the actuator 203 might be different from the reference value due to changes with time and variations in the apparatus upon moving the table section 101 downward as viewed in the vertical direction H, the amount of the fluid 231a is adjusted according to the past history to thereby control its pressure. Thus, the present embodiment makes it easy to smoothly move the table section 101 in a manner similar to the first embodiment. Similarly, even when the pressure based on the fluid 231a of the actuator 203 might be different from the reference value according to the weight of a subject to be imaged or photographed, it becomes easy to smoothly move the table section 101. Although there might be a case in which the weight of a subject has a trend to be constant as in the pediatrics department or the like in a medical field in particular, adjustments corresponding to the constant trend can be made in the present embodiment. Therefore, advantageous effects similar to the first embodiment can further be manifested.

<THIRD EMBODIMENT>

Figure 11:
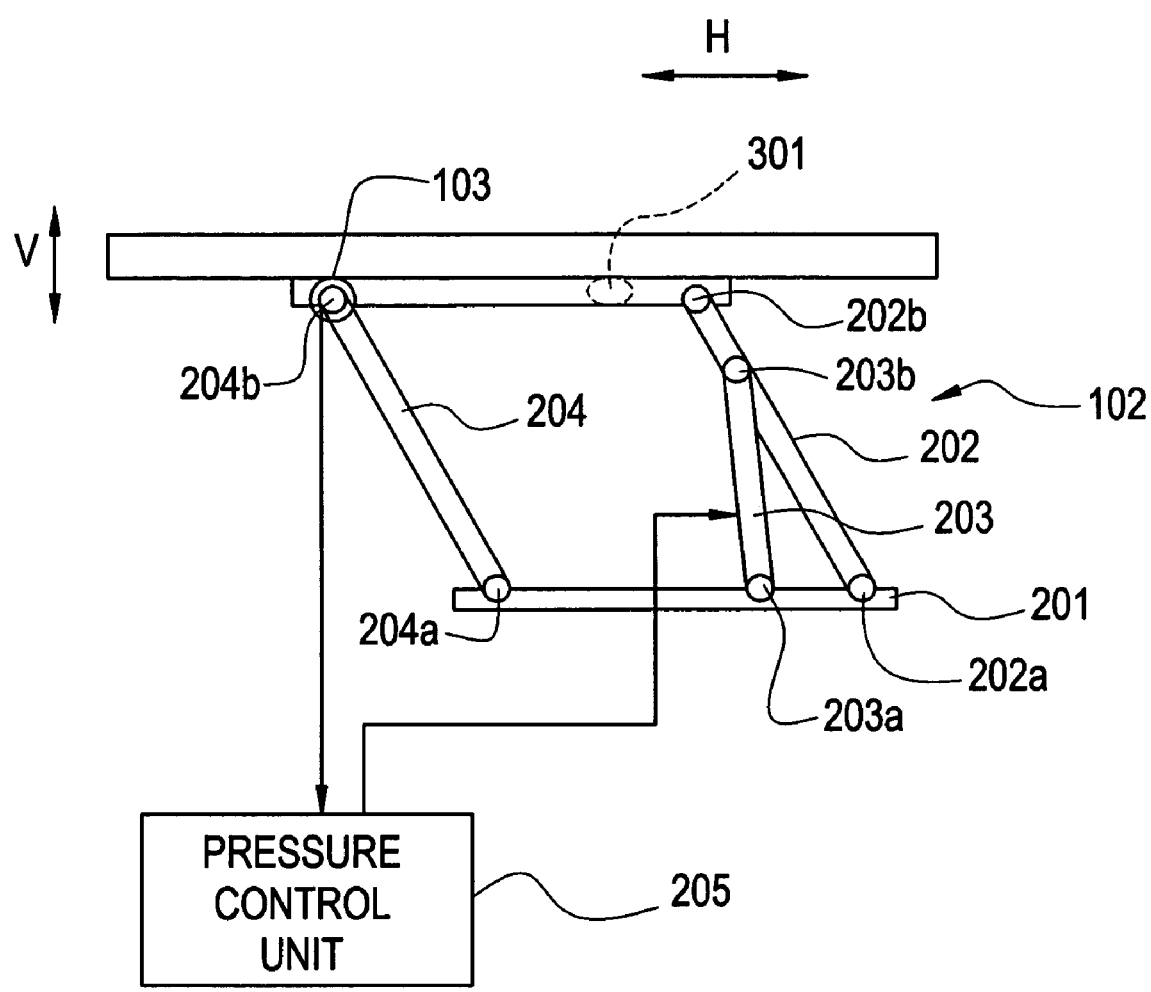
FIG. 11 is a block diagram showing the construction of a subject moving device in an X-ray CT apparatus of a third embodiment according to the present invention.

FIG. 11 is a block diagram showing the construction of a subject moving device 4 in an X-ray CT apparatus of a third embodiment according to the present invention.

As shown in FIG. 11, the present embodiment is similar to the first embodiment except that a position detection unit 103 of the subject moving device 4 differs. Therefore, dual components are given the same reference numerals and their explanations are omitted.

As shown in FIG. 11, the position detection unit 103 of the present embodiment is provided at a sixth shaft 204b of a second support bar 204 and includes an angle measuring instrument for measuring a tilt angle θ at which the second support bar 204 is inclined with respect to the horizontal direction. The angle measuring instrument of the position detection unit 103 measures a tilt angle using, for example, a rotary encoder. Here, the second support bar 204 is rotated with a rise in the table section with a table section 101 extending in the horizontal direction as the reference, and its inclined angle θ is measured. Then, the position detection unit 103 calculates a first position in a vertical direction, of the table section 101 on the basis of the tilt angle θ measured by the angle measuring instrument.

When an actuator 203 moves the table section 101 from the first position in the vertical direction H to a downward second position, a pressure control unit adjusts the amount of fluid 231*a* held in the actuator 203 on the basis of the first position of the table section 101 determined by the position detection unit 103 to thereby control pressure based on the fluid 231*a*.

According to the present embodiment, as described above, the pressure control unit adjusts the amount of the fluid 231*a* held in the actuator 203 on the basis of the first position of the table section 101 detected by the position detection unit 103 in a manner similar to the first embodiment to thereby control the pressure based on the fluid 231*a*. Therefore, the present embodiment can obtain advantageous effects similar to the first embodiment.

Incidentally, the present invention is not limited to the above embodiments upon implementation of the present invention. Various modifications can be adopted.

Although the present embodiment explains the example illustrative of the X-ray CT apparatus in which the scan section for scanning the subject has the radiation unit for applying radiation to the subject and the detection unit for detecting the radiation applied from the radiation unit and transmitted through the subject and thereby obtaining the row data of the image, the present invention is not limited to it. The present invention can be applied even to, for example, a magnetic resonance imaging apparatus wherein a radiation unit applies an electromagnetic wave to a subject lying in a static magnetic field, and a detection unit obtains a magnetic resonance signal from the subject as row data.

Although the above embodiment explains the example in which the X rays are used as the radiation applied by the radiation unit, the present invention is not limited to it. Radiation such as gamma rays or the like may be used.

Many widely different embodiments of the invention may be constructed without departing from the spirit and the scope of the present invention. It should be understood that the present invention is not limited to the specific embodiments described in the specification, except as defined in the appended claims.

The invention claimed is:

1. An imaging apparatus having a table unit supporting a subject and a table mover for moving the table unit to an imaging space and which images the subject supported by the table unit moved to the imaging space by the table mover, comprising:
    a position detector for detecting a position in a vertical direction, of the table unit,
    wherein the table mover includes,
    a bottom plate provided downward from the table unit as viewed in the vertical direction,
    a support bar having a first shaft provided at one end thereof, which is pivotally supported by the bottom plate, and a second shaft provided at the other end thereof, which is pivotally supported by the table unit, said support bar supporting the table unit,
    an actuator having a third shaft provided at one end thereof, which is pivotally supported by the bottom plate, and a fourth shaft provided at the other end thereof, which is pivotally supported by the support bar, said actuator expanding and contracting according to pressure of fluid held thereinside to thereby rotate the support bar with the first shaft as the center to move the table unit in the vertical direction, and
    a pressure controller for adjusting a flow rate of the fluid held in the actuator to thereby control pressure based on the fluid held in the actuator, and
    wherein when the actuator moves the table unit from a first position in the vertical direction to a downward second position, the position detector detects the first position where the movement of the table unit is started by the actuator, and the pressure controller adjusts the amount of the fluid held in the actuator on the basis of the first position detected by the position detector to thereby control the pressure.

2. The imaging apparatus according to claim 1,
    wherein the position detector detects a third position where the table unit is moved from the first position by the actuator, and
    wherein the pressure controller adjusts the amount of the fluid held in the actuator on the basis of an error at the time that the table unit is moved to the third position different from the second position as viewed in the vertical direction, thereby to control the pressure.

3. The imaging apparatus according to claim 2, further comprising:
    an error calculation unit for calculating the error at the time that the table unit is moved to the third position different from the second position as viewed in the vertical direction, from the result of detection by the position detector; and
    an error memory unit for storing the plurality of errors calculated by the error calculation unit therein,
    wherein the pressure controller adjusts the amount of the fluid held in the actuator on the basis of the errors stored in the error memory unit to thereby control the pressure.

4. The imaging apparatus according to claim 1, wherein the pressure controller has a proportional controlled valve which adjusts a flow rate at the time that the fluid held in the actuator is discharged, on the basis of each voltage supplied thereto.

5. The imaging apparatus according to claim 1, wherein the position detector includes an angle measuring instrument for measuring a tilt angle at which the support bar is inclined with respect to a horizontal direction and calculates the position in the vertical direction, of the table unit on the basis of the tilt angle measured by the angle measuring instrument.

6. The imaging apparatus according to claim 1, further including a scan section for scanning the subject moved to the imaging space,
    wherein the scan section includes:
    a radiation unit for irradiating the subject with radiation; and
    a detection unit for detecting the radiation applied from the radiation unit and transmitted through the subject.

7. The imaging apparatus according to claim 5, wherein the radiation unit applies X rays as the radiation.

8. A subject moving device comprising:
    a table unit for supporting a subject;
    a table mover for moving the table unit in a vertical direction; and
    a position detector for detecting a position in the vertical direction, of the table unit,
    wherein the table mover includes,
    a bottom plate provided downward from the table unit as viewed in the vertical direction,
    a support bar having a first shaft provided at one end thereof, which is pivotally supported by the bottom plate, and a second shaft provided at the other end thereof, which is pivotally supported by the table unit, said support bar supporting the table unit,
    an actuator having a third shaft provided at one end thereof, which is pivotally supported by the bottom plate, and a fourth shaft provided at the other end thereof, which is pivotally supported by the support bar, said actuator expanding and contracting according to pressure of fluid held thereinside to thereby rotate the support bar with the first shaft as the center to move the table unit in the vertical direction, and a pressure controller for adjusting a flow rate of the fluid held in the actuator to thereby control pressure based on the fluid held in the actuator, and wherein when the actuator moves the table unit from a first position in the vertical direction to a downward second position, the position detector detects the first position where the movement of the table unit is started by the actuator, and the pressure controller adjusts the amount of the fluid held in the actuator on the basis of the first position detected by the position detector to thereby control the pressure.

9. The subject moving device according to claim 8, wherein the position detector detects a third position where the table unit is moved from the first position by the actuator, and wherein the pressure controller adjusts the amount of the fluid held in the actuator on the basis of an error at the time that the table unit is moved to the third position different from the second position as viewed in the vertical direction, thereby to control the pressure.

10. The subject moving device according to claim 8, further comprising:

an error calculation unit for calculating the error at the time that the table unit is moved to the third position different from the second position as viewed in the vertical direction, from the result of detection by the position detector; and an error memory unit for storing the error calculated by the plurality of errors calculation unit therein, wherein the pressure controller adjusts the amount of the fluid held in the actuator on the basis of the errors stored in the error memory unit to thereby control the pressure.

* * * * *